United States Patent
Haensler

(10) Patent No.: US 6,610,308 B1
(45) Date of Patent: Aug. 26, 2003

(54) IMMUNOSTIMULANT EMULSION

(75) Inventor: Jean Haensler, Saint Genis les Ollières (FR)

(73) Assignee: Aventis Pasteur S.A., Lyon Cedex (FR)

(*) Notice: Subject to any disclaimer, the term of this patent is extended or adjusted under 35 U.S.C. 154(b) by 0 days.

(21) Appl. No.: 09/786,532

(22) PCT Filed: Sep. 13, 1999

(86) PCT No.: PCT/FR99/02177

§ 371 (c)(1),
(2), (4) Date: Jun. 27, 2001

(87) PCT Pub. No.: WO00/15256

PCT Pub. Date: Mar. 23, 2000

(30) Foreign Application Priority Data

Sep. 11, 1998 (FR) .............................. 98 11520

(51) Int. Cl.[7] .................. A61K 45/00; A61K 39/00; C07H 21/02
(52) U.S. Cl. ................ 424/278.1; 424/184.1; 424/283.1; 536/23.1
(58) Field of Search .......... 424/184.1, 204.1, 424/209.1, 211.1, 278.1, 283.1; 536/23.1

(56) References Cited

U.S. PATENT DOCUMENTS 5,908,777 A * 6/1999 Lee et al. ............ 435/320.1

FOREIGN PATENT DOCUMENTS

WO    WO 96/02555 A1 * 2/1996

OTHER PUBLICATIONS

Hacking, D. et al., Respiratory Syncytial Virus—Viral Biology and the Host Response, Journal of Infection (2002) 45:18–24.*

* cited by examiner

Primary Examiner—James Housel
Assistant Examiner—Stacy S. Brown
(74) Attorney, Agent, or Firm—McDonnell Boehnen Hulbert & Berghoff

(57) ABSTRACT

The invention concerns an oil-in-water immunostimulant emulsion comprising an aqueous phase and an oil phase, characterised in that it further comprises an immunostimulant polynucleotide whereof at least part is covalently bound to at least a lipid molecule. The invention also concerns a vaccine composition comprising such an emulsion as immunoadjuvant.

14 Claims, No Drawings

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthesized sequence

<400> SEQUENCE: 1
gagaacgctc gaccttcgat                                              20

<210> SEQ ID NO 2

-continued

```
<211> LENGTH: 20
<212> TYPE: DNA
<213> ORGANISM: Artificial Sequence
<220> FEATURE:
<223> OTHER INFORMATION: synthesized sequence

<400> SEQUENCE: 2 gggtcaagc ttgagggggg                                              20
```

IMMUNOSTIMULANT EMULSION

This application is a 371 of PCT/FR00/02177 filed Sep. 13, 1999, and claims priority to foreign application FR 98/11520 filed Sep. 11, 1998.

The invention relates to the domain of vaccines and more particularly to vaccine adjuvants.

Vaccines, whether they are prophylactic or therapeutic, are intended to stimulate the immune system of the human or animal organism to which they are administered, the response of the immune system possibly being either a response of the humoral type (production of antibodies), a response of cellular type, or a combination of the 2 types of response. Conventionally, for many years, vaccination has consisted in administering to an organism a nonpathogenic version of a microorganism so as to prepare the immune system to react effectively should the organism subsequently encounter the same microorganism, in its pathogenic version. The antigen administered during the vaccination can be of various types: whole or fragmented killed microorganism, attenuated live strain of the microorganism, antigenic fractions of the microorganism or polynucleotides capable of leading to the expression by the organism of an antigenic fraction.

For a long time already, attempts have been made to increase the response of the immune system or to modify its nature, not only by acting on the antigen administered or on its method of administration, but also by adding to it immunostimulating substances or adjuvants. Since Freund's complete adjuvant, many products have been tested, in particular inorganic salts (such as zinc chloride calcium phosphate, aluminum hydroxide or aluminum phosphate, for example), saponins, polymers, lipids or lipid fractions (Lipid A, Monophosphoryl Lipid A), etc. However, few of them have all the desired characteristics: to be good immunoadjuvants which are stable but have no risk of toxicity.

Oligonucleotides which may have immunostimulating activity are, on the other hand, known, through application WO 96/02555, these oligonucleotides possibly being administered as a vaccine adjuvant. This reference also mentions the possibility of combining with these oligonucleotides, by ionic or covalent attachment or by encapsulation, means for targeting the administration of the oligonucleotide. Such means can, in particular, consist of sterol, lipid (for example a cationic lipid, a virosome or a liposome) or an agent for specific binding to the target cell (for example a binder recognized by a receptor specific for the target cell). That application also mentions, among all the variants of use of the polynucleotides described, the possibility of administering them in conjunction with a pharmaceutically acceptable carrier vehicle. That application does not identify a vehicle as being of particular advantage, but gives an indicative list thereof and cites, in this respect, in particular solutions, solvents, dispersion media, delaying agents, emulsions and others, the use of such media for pharmaceutically active substances being mentioned as being well known in this domain.

According to the teaching of that document, the amount of oligonucleotides administered should be of sufficient amount to produce the desired biological effect.

Now, the authors of the present invention have found that, quite unexpectedly, it is possible to greatly increase the immunoadjuvant effect of an oligonucleotide without being obliged to increase the amount of oligonucleotides or the amount of antigens administered.

In order to attain this goal, a subject of the invention is an immunostimulant emulsion of the oil-in-water type, comprising at least one aqueous phase and one oily phase, characterized in that it also comprises at least one immunostimulant polynucleotide, at least one portion of which is covalently coupled to at least one lipid molecule.

For the purposes of the invention, the expression "emulsion of the oil-in-water type" is intended to mean a dispersion of droplets of oil in an aqueous phase which can consist of buffer such as the PBS buffer. The oily phase consists of a pharmaceutically acceptable oil which can be a mineral, animal or plant oil. Preferably, an oil which can be metabolized is used, such as squalene, esters (in particular ethyl oleate, isopropyl myristate), a plant oil (for example castor oil, sunflower oil, olive oil, etc.) or a modified plant oil (ex.: macrogol glycerides). It is possible, in particular, to obtain a satisfactory emulsion by mixing 500 mg of squalene with 10 ml of PBS buffer in a machine such as an ULTRA-TURRAX™, and then microfluidizing the dispersion obtained using a microfluidizer such as the Microfluidics™, which makes it possible to obtain oily particles which have a diameter of less than 200 nm.

In order to facilitate the formation of the emulsion, it is possible to also use a surfactant, in particular a surfactant which has an HLB (Hydrophilic/Lipophilic Balance) value of between 6 and 14. It is in particular possible to use a surfactant chosen from the following list of products: sorbitan esters and polysorbates, ethoxylated castor oil, which may or may not be hydrogenated, ethoxylated stearic acid, 10 EO oleyl alcohol, 20 EO cetostearyl alcohol, glycerol stearate, propylene glycol stearate, lecithins, sodium lauryl sulfate, sodium stearate, 7 EO ethoxylated glycerol cocoate, ethoxylated esters of glycerol, ethoxylated oleic acids, and mannitan oleate. Particularly good results have been obtained using TWEEN™ 80.

The emulsion obtained is considered to be immunostimulant if it is capable of causing or of increasing the stimulation of the immune system, for example when it is administered together with a vaccine antigen. In this application, the emulsion is used as an immunoadjuvant.

This immunoadjuvant activity may be expressed in various ways:
- make the response of the immune system to the joint administration of the antigen and of the emulsion visible, whereas the response to administration of the antigen alone was not,
- increase the degree of the response of the immune system without modifying the nature thereof (for example: increase the amount of antibodies produced),
- modify the nature of the response of the immune system to the administration of the antigen (for example, induce a cellular response, whereas the administration of the a alone caused only a humoral response),
- induce or increase the production of cytokines, or of certain cytokines in particular.

For the purpose of the present invention, the term "polynucleotides" is understood to mean a single-stranded oligonucleotide having from 6 to 100 nucleotides, preferably from 6 to 30 nucleotides. It can be an oligoribonucleotide or an oligodeoxy-ribonucleotide. Preference is given to the use of polynucleotides comprising basic sequences with inverted symmetry, such as is the case in palindromic sequences (i.e sequences of the type ABCDEEE'D' C' B' A' in which A and A', B and B', C and C', D and D', and E and E' are bases which are complementary in the sense of Watson and Crick), and more particularly polynucleotides comprising at least one cytosine, guanine dinucleotide sequence in which the cytosine and guanine are not methylated. Any other polynucleotide known to be, by its very nature, immunostimulant may be suitable for the purposes of the invention. Thus, it is also possible to use the immunostimulant oligonucleotides described in Patent Application WO96/02555. Particularly good results have been obtained using a polynucleotide for which the sequence of the bases is as follows: GAGAACGCTCGACCTTCGAT.

The oligonucleotides suitable for the purposes of the invention can be in the form of phosphodiesters or, in order to be more stable, in the form of phosphorothioates or of phosphodiester/phosphorothioate hybrids. Although it is possible to use oligonucleotides originating from existing nucleic acid sources, such as genomic DNA or cDNA, preference is given to the use of synthetic oligonucleotides. Thus, it is possible to develop oligonucleotides on a solid support using the β-cyanoethyl phosphoramidite method (Beaucage, S. L. and Caruthers, M. H. Tetrahedron Letters 22, 1859–1862 (1981)) for the 3'5' assembly, and then precipitation in ethanol in the presence of 0.3 M sodium acetate not adjusted for pH (0.3M final) is carried out. Next, precipitation with 4 volumes of 80% ethanol is carried out, followed by, drying before taking up the precipitate in pure water.

In the phosphorothioate-containing oligonucleotides, one of the oxygen atoms making up the phosphate group is replaced with a sulfur atom. Their synthesis can be carried out as previously described, except that the iodine/water/pyridine tetrahydrofuran solution which is used in the oxidation step required for the synthesis of the phosphodiester linkages is replaced with a TETD (tetraethylthiuram disulfide) solution which provides the sulfate ions allowing the phosphorothioate group to be produced.

It is also possible, to envisage other modifications of the phosphodiester linkages, of the bases or of the sugars, so as to modify the properties of the oligonucleotides used, and in particular so as to increase their stability.

According to the invention, at least one lipid molecule is covalently coupled to the polynucleotide. This lipid molecule is preferably a molecule of cholesterol or of a derivative of cholesterol. The coupling can be carried out by covalent attachment to one or to each end of the polynucleotide, or by insertion next to each base of at least one lipid molecule. This coupling can be carried out directly during the synthesis of the polynucleotide, using in the oligonucleotide synthesizer, a reagent such as cholesterol phosphoramidite instead of the phosphoramidite reagent conventionally used.

The antigens the effect of which it is possible to potentiate using the emulsion according to the present invention can be varied in nature; they can, in particular, be proteins, glycoproteins, glyco-conjugates, polyosides or pqlynucleotides comprising DNA fractions capable of causing the expression of molecules of interest; it can also be a mixture of various antigens. Particularly good results have been obtained with a composition comprising influenza antigens such as are present in the commercially available vaccine VAXIGRIP™.

It is possible to obtain an emulsion according to the invention by carrying out the following procedure: first of all, the oil is mixed, with stirring, with the aqueous phase optionally consisting of a buffer solution into which a surfactant has been incorporated. The mixture obtained is homogenized by means, for example, of a propellor mixer, in order to produce an emulsion of the oil-in-water type. Preferably, the emulsion obtained is then treated using a microfluidizer, in order to reduce the droplets of oil to a diameter of less than 200 nm.

Then, with this emulsion being maintained with stirring, the polynucleotide to which the lipid has been coupled is simply added to it and the emulsion which is the subject of the present invention is obtained.

When this emulsion is intended to be used as an immunoadjuvant, it is mixed, with stirring, with a composition comprising the antigen the potentiation of whose effect is desired. The mixture can be advantageously prepared in a volume ratio of 1. Next, it is possible to verify the unexpected effect and in particular the synergistic effect obtained on the stimulation of the immune system by the simultaneous use of a polynucleotide coupled to at least one lipid molecule and its incorporation into an emulsion of oil-in-water type.

To this end, it is possible to carry out an immunogenicity assay on mice divided into several groups, to which mice is administered, depending on the group:

either a composition comprising only the antigen or the mixture of antigens with respect to which it is desired to test the immunostimulant effect of the emulsion according to the invention, or a composition comprising the antigen or antigens of interest to which has been added a solution comprising only polynucleotides coupled to at least one lipid molecule, or a composition comprising the antigen or antigens of interest to which has been added an emulsion of oil-in-water type, without polynucleotide, or with a polynucleotide lacking immunostimulant activity with respect to the antigens administered, or a composition comprising the antigen or antigens of interest to which has been added an emulsion according to the invention.

For each of the mice immunized, it is then possible to determine the amount and nature of the antibodies produced, which makes it possible to determine the GMT (or Geometric Mean Titer of Antibodies); it is also possible to perform assays for the cytokines produced; in addition, it is possible to perform assays which enable the cellular response of the immune system to be determined.

The results obtained showed a considerable synergistic effect of the elements constituting the emulsion according to the invention.

In addition, the emulsion obtained according to the invention has increased stability with respect to emulsions of the same nature; i.e. those consisting of an identical aqueous phase and an identical oily phase, but lacking polynucleotides.

The examples which follow illustrate more specifically an embodiment of the invention.

EXAMPLE 1

Oligonucleotides are prepared using an automatic synthesizer machine supplied by Applied Biosystems, which uses the standard chemical phosphoramidite method and which comprises an oxidation step at each cycle.

This oxidation step is carried out by means of an iodine/water/tetrahydrofuran/acetonitrile solution in order to obtain a phosphodiester linkage, and by means of a tetraethylthiuram/acetonitrile solution in order to obtain a phosphorothioate linkage. An oligonucleotide 3 Db(S), the sequence of which is reproduced in SEQ ID NO 1, and which comprises phosphorothioate linkages throughout its length, is thus prepared.

An oligonucleotide MGC(S), the sequence of which is reproduced in SEQ ID NO 2, is also produced, which comprises both phosphodiester linkages and phosphorothioate linkages. The phosphorothioate linkages are located at each end; there are 2 phosphorothioate linkages in 3' and 5 phosphorothioate linkages in 5'. This oligonucleotide has no palindromic sequence, and in particular no CG sequence.

EXAMPLE 2

Oligonucleotides to which cholesterol molecules are coupled at the ends are prepared. The synthesis of these oligonucleotides 3 Db(S)-chol and MGC(S)-chol is carried out in the same way as in Example 1, with the exception of the phosphoramidite reagent, which is replaced with a specific reagent, Cholesterol-ON™ phosphoramidite, supplied by the company CLONTECH Lab. Inc., (USA), during the first and last cycle of synthesis, in order to obtain a cholesterol molecule inserted before each of the end nucleotides.

The nucleotide sequences obtained are identical to those of the oligonucleotides described in the previous example.

EXAMPLE 3

25 mg of Tween™80 and 500 mg of squalene are added to 10 ml of PBS buffer. The mixture obtained is emulsified using an ULTRA-TURRAX™ 25 apparatus for 1 min. at 13500 rpm.

The emulsion obtained is then fluidized using a 5-cycle treatment at 500 Psi in a Microfluidics™ microfluidizer.

EXAMPLE 4

Preparation of a Squalene/PBS Emulsion Comprising Polynucleotides Coupled to Cholesterol An immunostimulant emulsion according to the invention is prepared by mixing 435 µl of the solution (at 2.3 g/l) of 3 Db(S) coupled to cholesterol obtained in Example 2 (i.e. 1 mg of oligonucleotide), with 2 ml of the squalene/PBS emulsion obtained in Example 3, maintained with stirring.

Another emulsion is prepared by mixing 263 µl of the solution (at 3.81 g/l) of MGC(S) coupled to cholesterol obtained in Example 2 (i.e. 1 mg of oligonucleotide), with 2 ml of the squalene/PBS emulsion obtained in Example 3, maintained with stirring.

EXAMPLE 5

Preparation of the Immunization Compositions

Doses of immunization of various natures are prepared by adding, with stirring, 2 ml of split vaccine against influenza NIB16 (monovalent A/Singapore H1N1) containing 100 µg of hemagglutinin HA in-PBS buffer to 2 ml of each of the following preparations:

PBS buffer
MGC(S) solution obtained in Example 1,
MGC(S)-chol solution obtained in Example 2,
MGC(S)-chol emulsion obtained in Example 4,
3 Db(S) solution obtained in Example 1,
3 Db(S)-chol solution obtained in Example 2,
3 Db(S)-chol emulsion obtained in Example 2.

EXAMPLE 6

Immunization

Groups of six 6 to 8-week-old female Balb/c mice are used, each group corresponding to one of the preparations produced in Example 6. Each of the mice is immunized with 200 $\mu$l of the preparation corresponding to its group, and therefore receives 5 $\mu$g of HA per immunization, each mouse being immunized twice, with a 3 week interval, with the same preparation.

2 weeks after the second injection, the anti-HA specific antibody response is measured using an ELISA assay, and the GMT is determined for the IgG1s and for the IgG2as.

The results obtained are given below:

| | GMT/lgG1 | GMT/lgG2a |
|---|---|---|
| HA only | 38 062 | 2 137 |
| HA/MGC (S) | 37 518 | 1 050 |
| HA/MGC (S)-chol | 28 039 | 1 498 |
| HA/MGC (S)-chol/emulsion | 264 776 | 26 981 |
| HA/3 Db (S) | 63 939 | 43 529 |
| HA/3 Db (S)-chol | 65 904 | 31 066 |
| HA/3 Db (S)-chol/emulsion | 611 301 | 218 142 |

The results obtained confirm that the oligonucleotide 3 Db(S) clearly has immunostimulant properties since it is capable of inducing an increase in the antibody response with respect to that which is obtained during the administration of the antigens alone. On the other hand, the results obtained with the oligonucleotide MGC(S) do not show any immunostimulant activity.

In addition, it is observed that, unexpectedly, the emulsion containing an immunostimulant polynucleotide such as the; polynucleotide 3 Db(s) causes an antibody production which is clearly greater than that obtained with an emulsion containing the polynucleotide MGC(S-)l-chol; this effect is even more remarkable with regard to the production of IgG2a, which is an indication of the immune response being directed toward a TH1-type response, this direction being sometimes desired in certain vaccinial targets.

In fact, if it is considered that the expected effect of an emulsion is the effect obtained with the emulsion HA/MGC (S)-chol (the oligonucleotide MGC(S) having, on its own, no immunostimulant effect with respect to the antigens administered, as is analyzed above), a considerable synergistic effect of the emulsion according to the invention is noted, since the titer obtained for the production of antibodies, whether for IgG1s or, even more clearly, for IgG2as, is clearly higher than the sum of the titers obtained separately for each of the 2 compositions (emulsion HA/MGC(S) on the one hand and solution HA/3 Db(S) on the other).

EXAMPLE 7

Vaccine compositions are prepared comprising the following elements:
  subunit antigens against the RSV (or Respiratory Syncitial Virus) in the presence of aluminum gel, in a proportion of 1 μgram of total proteins (proteins F, G and M) in PBS buffer or supplemented, depending on the case, with the folllowing elements:
  solution,3 Db(S) obtained in Example 1,
  emulsion 3 Db(S) obtained in Example 4,
  emulsion MGC(S) obtained in Example 4.
The doses are 50 μliters and comprise 50 micrograms of oligonucleotides.

These compositions are administered to mice on D0 and on D28; 5 to 6 weeks after the booster injection, the spleens of the mice are removed in order to evaluate the amount of γ-interferon produced.

The following results are obtained, after ELISA assay carried out after secondary restimulation in vitro:

|  | Amount of interferon in pg/ml |
|---|---|
| Antigens + aluminum adjuvant | 3432 |
|  | 2565 |
|  | 2998 |
| Antigens + aluminum adjuvant + 3 Db(S) | 13400 |
|  | 9543 |
|  | 1147 |
| Antigens + aluminum adjuvant + emulsion MGC(S) | 5130 |
|  | 9216 |
|  | 7173 |
| Antigens + aluminum adjuvant + emulsion according to the invention | 57394 |
|  | 42285 |
|  | 49839 |

These results clearly show the synergy obtained by using an immunostimulant oligonucleotide and an emulsion according to the invention, when the RSV is used and the production of γ-interferon, which is a good indicator of the TH1 response, is observed.

EXAMPLE 8

Immunization doses are prepared which are identical to those of Example 7, with the exception of the RSV antigens, which are not in the presence of aluminum gel. The 50-μliter doses are administered intramuscularly to groups of 6 mice.

4 weeks after immunization, the mice are bled and the levels of anti-protein F antibodies are determined by ELISA titering. The results obtained are given in the following table:

|  | IgG | IgG1 | IgG2a |
|---|---|---|---|
| Antigens + PBS | 100 | 100 | 100 |
|  | 100 | 100 | 100 |
|  | 100 | 100 | 100 |
|  | 100 | 100 | 100 |
|  | 100 | 100 | 100 |
| Antigens + 3 Db(S) | 6400 | 400 | 6400 |
|  | 6400 | 400 | 12800 |
|  | 12800 | 800 | 6400 |
|  | 6400 | 400 | 3200 |
|  | 3200 | 100 | 25600 |
|  | 6400 | 400 | 25600 |
| Antigens + emulsion MGC(S) | 12800 | 1600 | 6400 |
|  | 6400 | 400 | 100 |
|  | 51200 | 6400 | 100 |
|  | 25600 | 1600 | 100 |
|  | 25600 | 1600 | 100 |
| Antigens + emulsion according to the invention | 25600 | 1600 | 25600 |
|  | 12800 | 400 | 12800 |
|  | 51200 | 1600 | 25600 |
|  | 102400 | 6400 | 1600 |
|  | 51200 | 3200 | 25600 |

These results confirm the advantage of using an emulsion according to the invention when the antigens are the antigens of the Respiratory Syncitial Virus.

---

What is claimed is:

1. An immunostimulant emulsion of the oil-in-water type, comprising at least one aqueous phase and one oily phase, and further comprising at least one immunostimulant polynucleotide, at least one portion of which is covalently coupled to at least one lipid molecule.

2. The emulsion as claimed in claim 1, wherein the lipid molecule is a cholesterol molecule.

3. The emulsion as claimed in claim 1, wherein the immunostimulant polynucleotide comprises at least one palindromic sequence.

4. The emulsion as claimed in claim 1, wherein the immunostimulant polynucleotide is a phosphodiester, phosphorothioate or phosphodiester phosphorothioate hybrid oligodeoxynucleotide.

5. The emulsion as claimed in claim 1, wherein the immunostimulant polynucleotide comprises SEQ. ID. NO. 1.

6. The emulsion as claimed in claim 1, wherein the portion coupled to the at least one lipid molecule is located at the 5' end of the polynucleotide.

7. The emulsion as claimed in claim 1, further comprising at least one surfactant.

8. The emulsion as claimed in claim 8, wherein the surfactant is polyoxyethylenesorbitan monooleat.

9. The emulsion as claimed in claim 1, wherein the oily phase comprises squalene.

10. A composition comprising at least one antigen and an immunostimulant emulsion as claimed in claim 1.

11. The composition as claimed in claim 10, comprising at least one antigen against influenza.

12. The composition as claimed in claim 10, comprising at least one antigen of the Respiratory Syncitial Virus.

13. A method of stimulating the immune system of a mammal, the method comprising administering an emulsion according to claim 1.

14. A method of enhancing an immune response in a mammal to the antigen of claim 10 comprising administering the composition of claim 10.

* * * * *